(12) United States Patent
Adams et al.

(10) Patent No.: US 12,048,785 B2
(45) Date of Patent: Jul. 30, 2024

(54) DRY FOG GENERATOR

(71) Applicant: Pure Maintenance, Layton, UT (US)

(72) Inventors: Brandon Adams, Layton, UT (US); Mike Adams, Layton, UT (US)

( * ) Notice: Subject to any disclaimer, the term of this patent is extended or adjusted under 35 U.S.C. 154(b) by 747 days.

(21) Appl. No.: 17/216,663

(22) Filed: Mar. 29, 2021

(65) Prior Publication Data

US 2022/0111103 A1     Apr. 14, 2022

Related U.S. Application Data

(60) Provisional application No. 63/091,295, filed on Oct. 13, 2020.

(51) Int. Cl.
*A61L 9/14* (2006.01)
*A61L 101/36* (2006.01)

(52) U.S. Cl.
CPC ............. *A61L 9/14* (2013.01); *A61L 2101/36* (2020.08); *A61L 2209/111* (2013.01); *A61L 2209/134* (2013.01)

(58) Field of Classification Search
CPC .......... A61L 9/00; A61L 9/14; A61L 2101/00; A61L 2101/32; A61L 2101/36; A61L 2209/00; A61L 2209/10; A61L 2209/11; A61L 2209/111; A61L 2209/13; A61L 2209/134; A61L 2209/135; B05B 7/00; B05B 7/24; B05B 7/2489; B05B 12/00; B05B 12/08; B05B 12/12; B05B 12/14; B05B 12/1472; F24F 6/00; F24F 6/12; F24F 8/00; F24F 8/20; F24F 8/24; F24F 2006/00; F24F 2006/12; F24F 2006/14; F24F 2006/143; F24F 2110/00; F24F 2110/20

See application file for complete search history.

(56) References Cited

U.S. PATENT DOCUMENTS

| | | |
|---|---|---|
| 5,699,786 A | 12/1997 | Oshima et al. |
| 5,884,808 A | 3/1999 | Muderlak et al. |
| 6,973,975 B1 | 12/2005 | Adamson et al. |
| 9,238,239 B2 * | 1/2016 | Adams ............... B05B 7/0416 |
| 10,369,242 B1 * | 8/2019 | Kellogg, Jr. ............ F24F 11/75 |
| 2006/0231644 A1 | 10/2006 | Breedlove et al. |
| 2013/0140374 A1 | 6/2013 | Adams et al. |
| 2016/0303590 A1 | 10/2016 | Collins |
| 2018/0311707 A1 * | 11/2018 | Taylor ................. H01J 37/3244 |

(Continued)

OTHER PUBLICATIONS

Rodriquez "PCT International Search Report for International Application No. PCT/US2021/054829" mailed Jul. 18, 2022, 4 pages.

(Continued)

*Primary Examiner* — Natasha E Young
(74) *Attorney, Agent, or Firm* — Intellectual Strategies (57) ABSTRACT

An apparatus, system, and method are disclosed for dry fogging system. The system includes a first liquid tank including compressed air and a first liquid configured to disinfect and sterilize. The system further includes a second liquid tank including a second liquid. The system further includes a control panel configured to regulate dispensing of the first liquid and the second liquid. The first liquid tank, the second liquid tank, and the control panel are modular and configured to detach.

20 Claims, 5 Drawing Sheets

(56) References Cited

U.S. PATENT DOCUMENTS

2019/0118203 A1    4/2019   Fontaine et al.

OTHER PUBLICATIONS

Rodriquez "Written Opinion of the International Searching Authority for International Application No. PCT/ US2021/054829" mailed Jul. 18, 2022, 9 pages.

Lindner "International Preliminary Report on Patentability for International Application No. PCT/US2021/054829" mailed Apr. 27, 2023, 10 pages.

* cited by examiner

```
                          300 ─┐                          ┌─ 302
                               ▼                         ╱
                    ┌─────────────────────────────┐
                    │ Connecting a first modular  │
                    │ liquid tank and a second    │
                    │ modular liquid tank to a    │
                    │ control panel               │
                    └─────────────────────────────┘
                                  │                       ┌─ 304
                                  ▼                      ╱
                    ┌─────────────────────────────┐
                    │ Forcing compressed air and  │
                    │ aerosolized sterilant from  │
                    │ the first modular liquid    │
                    │ tank through a nozzle on    │
                    │ the control panel           │
                    └─────────────────────────────┘
                                  │                       ┌─ 306
                                  ▼                      ╱
                    ┌─────────────────────────────┐
                    │ Forcing aerosolized         │
                    │ antimicrobial through the   │
                    │ nozzle on the control panel │
                    └─────────────────────────────┘
                                  │
                                  ▼
                           ╱─────────────╲
                          (  Method ends  )
                           ╲─────────────╱
```

DRY FOG GENERATOR

RELATED APPLICATIONS

This application claims the benefit of U.S. Provisional Patent Application No. 63/091,295, filed Oct. 13, 2020, which is incorporated herein by reference in its entirety.

FIELD

This invention relates to indoor air remediation and more particularly relates to a fogging module for treating, remediating, disinfecting, or sterilizing indoor air environments.

BACKGROUND

The need for clean, healthy, and treated air is increasing. With advances in technology comes the need to provide indoor air environments that are suitable for many different situations and technology to treat, remediate, disinfect, and sterilize indoor air environments. Treating, remediating, disinfecting, or sterilizing indoor air environments needs to be economical, sustainable, and convenient to be adopted on a large scale. Many conventional systems are restricted in their ability to satisfy these conditions.

SUMMARY

The subject matter of the present application has been developed in response to the present state of the art, and in particular, in response to the problems and disadvantages associated with conventional systems that have not yet been fully solved by currently available techniques. Accordingly, the subject matter of the present application has been developed to provide embodiments that overcome at least some of the shortcomings of prior art techniques.

Disclosed herein is a system. The system includes a first liquid tank including compressed air and a first liquid configured to disinfect and sterilize. The system further includes a second liquid tank including a second liquid. The system further includes a control panel configured to regulate dispensing of the first liquid and the second liquid. The first liquid tank, the second liquid tank, and the control panel are modular and configured to detach. The preceding subject matter of this paragraph characterizes example 1 of the present disclosure.

The control panel further includes a liquid port, wherein the liquid port is configured to dispense an aqueous form of the first liquid. The preceding subject matter of this paragraph characterizes example 2 of the present disclosure, wherein example 2 also includes the subject matter according to example 1, above.

The control panel further includes a liquid port, wherein the liquid port is configured to dispense an aqueous form of the first liquid and an aqueous form of the second liquid. The preceding subject matter of this paragraph characterizes example 3 of the present disclosure, wherein example 3 also includes the subject matter according to any one of examples 1-2, above.

The control panel is configured to measure air pressure in the first liquid tank. The preceding subject matter of this paragraph characterizes example 4 of the present disclosure, wherein example 4 also includes the subject matter according to any one of examples 1-3, above.

The control panel is configured to measure air pressure within the first liquid tank. The preceding subject matter of this paragraph characterizes example 5 of the present disclosure, wherein example 5 also includes the subject matter according to any one of examples 1-4, above.

The control panel is configured to measure air pressure within the second liquid tank. The preceding subject matter of this paragraph characterizes example 6 of the present disclosure, wherein example 6 also includes the subject matter according to any one of examples 1-5, above.

The control panel is configured to regulate air pressure and liquid tank pressure independent of each other. The preceding subject matter of this paragraph characterizes example 7 of the present disclosure, wherein example 7 also includes the subject matter according to any one of examples 1-6, above.

The control panel is lined internally with heat tape. The preceding subject matter of this paragraph characterizes example 8 of the present disclosure, wherein example 8 also includes the subject matter according to any one of examples 1-7, above.

The first liquid tank and the second liquid tank are independently regulated by the control panel. The preceding subject matter of this paragraph characterizes example 9 of the present disclosure, wherein example 9 also includes the subject matter according to any one of examples 1-8, above.

The control panel is configured to be connected to a plurality of modular liquid tanks, wherein the first liquid tank and the second liquid tank are modular liquid tanks. The preceding subject matter of this paragraph characterizes example 10 of the present disclosure, wherein example 10 also includes the subject matter according to any one of examples 1-9, above.

The first liquid is a sterilant configured to disinfect and sterilize. The preceding subject matter of this paragraph characterizes example 11 of the present disclosure, wherein example 11 also includes the subject matter according to any one of examples 1-10, above.

The second liquid is a liquid antimicrobial. The preceding subject matter of this paragraph characterizes example 12 of the present disclosure, wherein example 12 also includes the subject matter according to any one of examples 1-11, above.

Disclosed herein is an apparatus for generating fog. The apparatus includes a control panel configured to regulate a dispensing of an aerosolized or aqueous substance. The system further includes a second liquid tank including a second liquid. The apparatus further includes a liquid port on the control panel configured to connect to at least one modular liquid tank and dispense the aerosolized or aqueous substance from the at least one modular liquid tank. The apparatus includes an air port on the control panel configured to dispense a gas. The gas may be compressed air. The control panel is configured to dispense the aqueous or aerosolized substance in combination with compressed air from the air port. The preceding subject matter of this paragraph characterizes example 13 of the present disclosure.

The liquid port on the control panel is configured to connect to at least two modular liquid tanks. The preceding subject matter of this paragraph characterizes example 14 of the present disclosure, wherein example 14 also includes the subject matter according to example 13, above.

The aerosolized substance is produced by combining controllable air pressure and controllable liquid pressure. The aerosolized substance comprises peracetic acid. The preceding subject matter of this paragraph characterizes example 15 of the present disclosure, wherein example 15 also includes the subject matter according to any one of examples 13-14, above.

The liquid port is configured to dispense aerosolized or aqueous substance from more than one modular liquid tank. The preceding subject matter of this paragraph characterizes example 16 of the present disclosure, wherein example 16 also includes the subject matter according to any one of examples 13-15, above.

The control panel is configured to modularly connect to a plurality of liquid tanks, wherein the control panel is further configured to independently regulate each of the plurality of liquid tanks. The preceding subject matter of this paragraph characterizes example 17 of the present disclosure, wherein example 17 also includes the subject matter according to any one of examples 13-16, above.

The control panel is configured to modularly connect to a plurality of liquid tanks, wherein the control panel is further configured to regulate air and liquid pressure in the first liquid tank and liquid pressure in the second liquid tank. The preceding subject matter of this paragraph characterizes example 18 of the present disclosure, wherein example 18 also includes the subject matter according to any one of examples 13-17, above.

The control panel further comprises a remote humidity detector or a ppm detector. The preceding subject matter of this paragraph characterizes example 19 of the present disclosure, wherein example 19 also includes the subject matter according to any one of examples 13-18, above.

Disclosed herein is a system. The system includes a first liquid tank including compressed air and a first liquid configured to disinfect and sterilize. The system further includes a second liquid tank including a second liquid. The system further includes a control panel configured to regulate dispensing of the first liquid and the second liquid. The control panel further comprises a liquid port, wherein the liquid port is configured to dispense an aerosolized form of the first liquid and the second liquid. The first liquid tank, the second liquid tank, and the control panel are modular and configured to detach. The preceding subject matter of this paragraph characterizes example 20 of the present disclosure.

A method is disclosed. The method includes connecting a first modular liquid tank and a second modular liquid tank to a control panel, wherein the first modular liquid tank comprises compressed air and a first liquid configured to disinfect and sterilize, and wherein the second modular liquid tank comprises a second liquid. The method further includes forcing compressed air and the first liquid, in aerosolized form, through a port on the control panel and forcing the second liquid, in aerosolized form, through the port on the control panel. The preceding subject matter of this paragraph characterizes example 21 of the present disclosure.

The forcing the compressed air and the first liquid through the port occurs before the forcing the second liquid through the port. The preceding subject matter of this paragraph characterizes example 22 of the present disclosure, wherein example 22 also includes the subject matter according to example 21, above.

The method includes independently regulating pressure in the first modular liquid tank and the second modular liquid tank with the control panel. The preceding subject matter of this paragraph characterizes example 23 of the present disclosure, wherein example 23 also includes the subject matter according to any one of examples 21-22, above.

The method includes detaching one of the first modular liquid tank or the second modular liquid tank from the control panel. The preceding subject matter of this paragraph characterizes example 24 of the present disclosure, wherein example 24 also includes the subject matter according to any one of examples 21-23, above.

The method includes connecting a plurality of modular liquid tanks to the control panel. The preceding subject matter of this paragraph characterizes example 25 of the present disclosure, wherein example 25 also includes the subject matter according to any one of examples 21-24, above.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Figure 1:
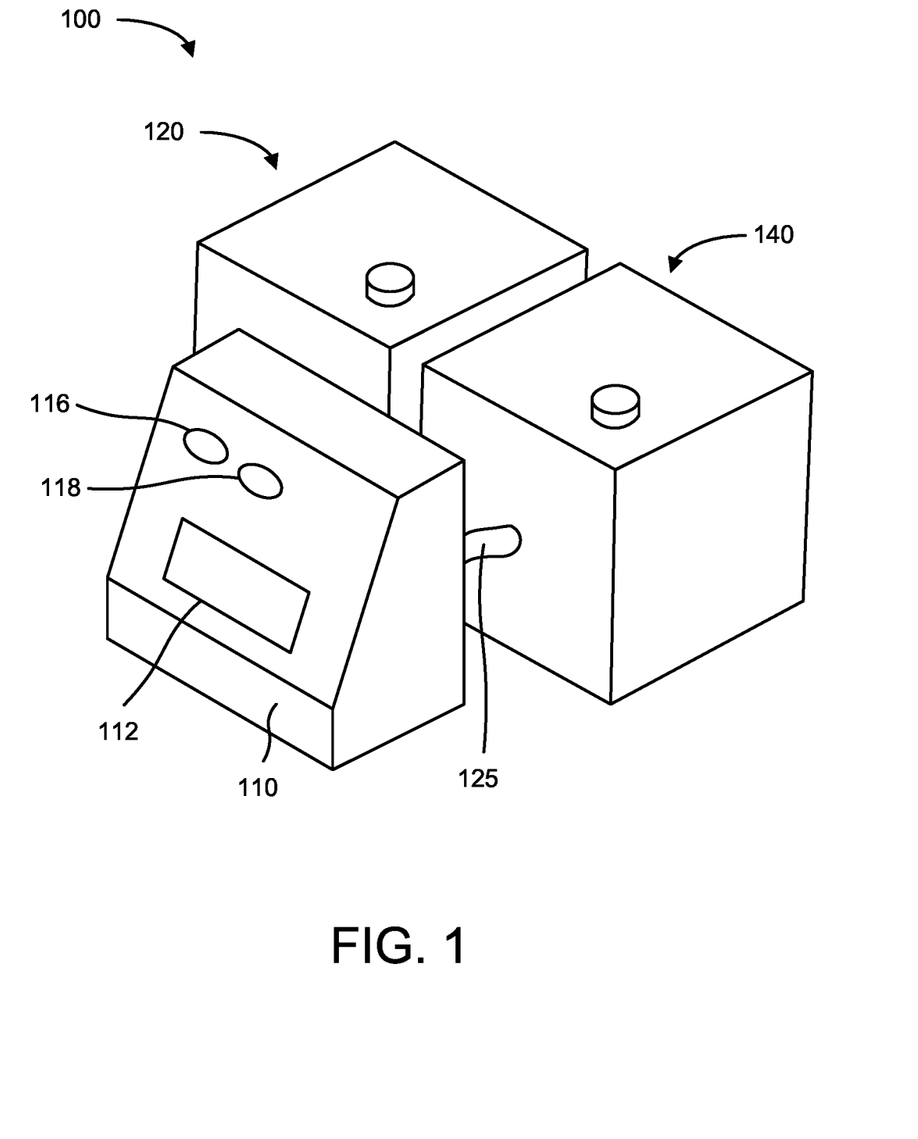
FIG. 1 is a schematic diagram illustrating an isometric view of an embodiment of a system for dry fogging in accordance with one or more embodiments of the present invention.

Referring to FIG. 1, an embodiment of a system 100 for dry fogging is shown. Although shown and described with certain components and functionality, other embodiments may include fewer or more components to implement less or more functionality. The system 100 includes a control panel 110, a first liquid tank 120, and a second liquid tank 140.

The liquid tanks (first liquid tank 120 and second liquid tank 140) are, in the illustrated embodiment, similar in size and shape and material, differing in only contents within their respective tanks. In some embodiments, the liquid tanks are different in size or shape allowing one or the other to provide more liquid for use. This may depend on the size and/or scope of use. The liquid tanks are configured to attach and detach from the control panel 110. In some embodiments, the liquid tanks are modular. Modular components allow for their attachment and detachment to allow for ease in configuring the system 100, replacing components, shipping, servicing, and operating. If either of the liquid tanks require service, they can be detached and the system 100 can operate on the remaining liquid tank or a replacement tank.

In some embodiments, the liquid tanks are made of stainless steel or another material that is suitable for the contents in the tank. In some embodiments, the contents of the tank may include compressed air, a sterilant, an antimicrobial, or microbicide. The contents of the tanks may vary depending on the application needed. In addition, the number of tanks that are modularly connected to the control panel 110 may vary. The control panel 110 may be configured to dispense the contents of the tanks in a sequential manner or at the same time. The control panel 110 may, in some embodiments, be configured to change the order of dispensing of the tanks.

In previous embodiments, the nozzle, port, or dispensing mechanism has been located on the tanks themselves. In some embodiments described herein, the control panel 110 includes a port, nozzle, or dispensing mechanism that is in communication with the contents of the tank such that the contents of the tank are aerosolized and dispensed from the port, nozzle, or dispensing mechanism.

In some embodiments, the two tanks include only a single delivery port. There may be a selector switch and/or valve to allow a user to select which tank is delivered to the delivery port. In some embodiments, the system includes tubing that runs from the control panel or the tanks. The length of the tubing can vary from a few feet to hundreds of feet. In some embodiments, the tubing is 100 feet. One tube is for delivery of compressed air and a second tube is for liquid delivery, in some embodiments. Fog is created at a collision of the air and the liquid at location just beyond a fog head cap (located at the end of the tubing). Control of the pressure of each of the liquid and the air, independently, allows for controlling the creation of the fog beyond the fog head cap. In some embodiments, the tubing has a diameter of ⅜ inch. Other diameters are contemplated. In some embodiments, at the end of the 100 foot tubing, the diameter may be reduced to, for example, ¼ inch for a short distance before the fog head caps.

In some embodiments, the tank is merely a reservoir for storing the sterilant or antimicrobial. In some embodiments, the control panel 110 is configured to aerosolize the contents of the tank within the tank. In some embodiments, the control panel 110 is configured to aerosolize the contents of the tank within the control panel 110 prior to dispensing through the port, nozzle, or dispensing mechanism.

In some embodiments, the liquid tanks include risers located at a bottom of the tanks and near a rear portion of the tank. The risers can be welded to the tanks. The risers are configured to slope the tanks such that liquid flows to the front of the tank.

In some embodiments, the liquid tanks are configured to be mechanically connected to the control panel 110. The control panel 110 includes valves, conduits, and other components that allow for the mixture of, the separating of, or the compartmentalizing of the contents from the various tanks. As such, the control panel 110 is, in some embodiments, configured to dictate the desired mixture of contents, the order of dispensing the contents, or the separation of dispensing of the contents of the liquid tanks.

In some embodiments, the control panel 110 includes various components that are configured to monitor the liquid tanks and their contents. In some embodiments, the control panel is configured to measure the pressure of the contents of the liquid tanks. This may include the air pressure or liquid pressure of the contents of the liquid tanks. In some embodiments, the control panel 110 regulates the pressure of the contents of the liquid tanks. The control panel 110 is configured to independently regulate the pressure of the individual liquid tanks.

In some embodiments, the control panel 110 includes one or more ports. As described earlier, the ports may be a nozzle or dispensing mechanism through which the aerosolized contents are dispensed from the control panel 110. The contents of the liquid tanks are aerosolized and travel from the particular tank through conduits and valves to the control panel 110 and are dispensed from the port on the control panel 110. In some embodiments, the control panel 110 includes a single port and is configured to funnel and direct the contents out the single port no matter from which liquid tank the contents are coming.

In some embodiments, the control panel 110 includes a plurality of ports. Each port may be configured to only dispense from a single designated liquid tank, or each port may be configured to dispense from all or some of the liquid tanks and is dictated by the control panel 110.

In some embodiments, the control panel 110 includes a liquid port 116 and an air port 118. The liquid port is configured to dispense in aerosolized form, the liquid contents of the liquid tanks. When more than one liquid tank is used, the liquid port, in some embodiments, will be configured to dispense the contents of the plurality of tanks. The air port 118 may be configured to dispense gases such as air. The air port 118 may be configured to supply air or a gas at anywhere between 1 and 140 psi, inclusive. The liquid port 116 may also be configured to supply liquid at similar pressures. In some embodiments, the liquid port 116 is configured to supply liquid at anywhere between 1 and 15 psi, inclusive.

In some embodiments, the system may include conduits 125 which are configured to fluidly connect the liquid port 116 to the internal reservoir of the liquid tanks.

In some embodiments, the control panel 110 includes a user interface 112 that is configured to allow a user to input conditions and manually operate the control panel 110 including the sequence of operation, the flow rate, the flow time, the concentration levels of sterilant, sanitizer, disinfectant, or antimicrobial that will be dispensed from the control panel 110. In some embodiments, these determinations are made automatically depending on the operating conditions of the system. Such factors including but not limited to the room size, the humidity, the temperature, the pressure, and the level of disinfecting needed may dictate the operating conditions of the system and may be automatically monitored and set based on an algorithm programmed into the control panel 110.

Figure 2:
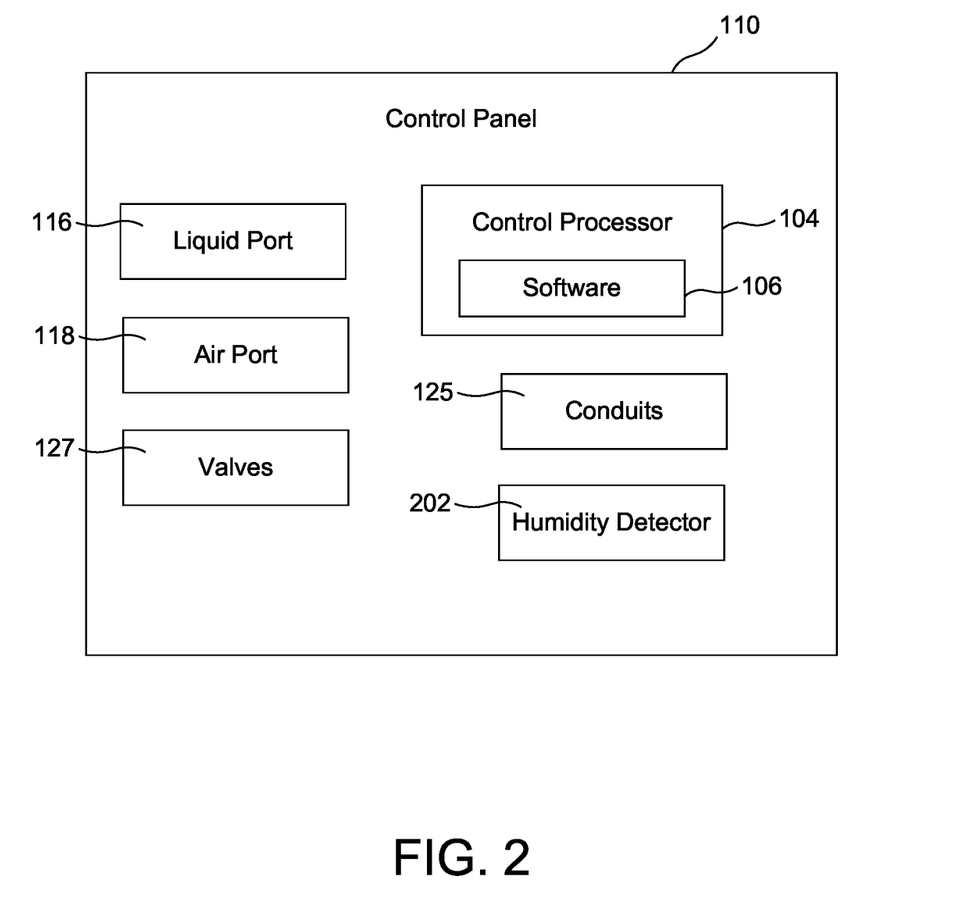
FIG. 2 is a schematic diagram illustrating an embodiment of a control panel in accordance with one or more embodiments of the present invention

Referring now to FIG. 2, a schematic diagram of a control panel 110 is shown. Although shown and described with certain components and functionality, other embodiments may include fewer or more components to implement less or more functionality.

The control panel 110 includes a control processor 104 and software 106. The control processor 104 is generally configured to control operations of the system 100 and the control panel 110, either alone or in conjunction with various processing sub-systems including the tanks and valves etc. of the overall system 100. For example, the control processor 104 might communicate electronically with the subsystems of the control panel 110 and the liquid tanks (see, for example, 120 and 140 of FIG. 1), as well as other any other system(s) included in various embodiments of the system 100.

The control processor 104 also includes software 106, in some embodiments, stored on any form of computer readable medium and accessible for execution by the control processor 104. The exact form or format of the software 106 is not constrained other than to be capable of performing the functions described herein and related functions within the scope of similar devices. In particular, the software 106 may be capable of carrying out part or all of the functionality described in any methods, steps, processes, or other functional descriptions of the system 100 and its component sub-systems.

In some embodiments, the control panel 110 includes a single or multiple ports. In the illustrated embodiment, the control panel 110 includes a liquid port 116 and an air port 118. As discussed previously, the liquid port 116 is configured to dispense in aerosolized form, the liquid contents of liquid tanks that are modularly connected to the control panel 110. When more than one liquid tank is used, the liquid port 116, in some embodiments, will be configured to dispense the contents of the plurality of tanks. The air port 118 may be configured to dispense gases such as air and may be connected separately to an air compressor.

In some embodiments, the control panel 110 further includes various valves 127 and conduits 125 that are configured to funnel the contents of the liquid tanks to the liquid port 116 and the air port 118 for dispensing. Although not described in detail, the valves 127 and conduits 125 may be configured to allow the control panel 110 to dispense the contents of a plurality of liquid tanks through a single liquid port 116. In other embodiments, the control panel 110 may have more than one liquid port 116 for dispensing the contents of the liquid tanks.

The effectiveness and running time of the overall system may be affected by the ambient operating conditions including, but not limited to, the humidity of the room. In some embodiments, the control panel 110 includes a humidity detector 202 or hygrometer or other similar device that is configured to measure the humidity of the room in which the system is operating. In some embodiments, the control panel 110 is configured to automatically change the parameters of operation depending on the humidity measured.

Figure 3:
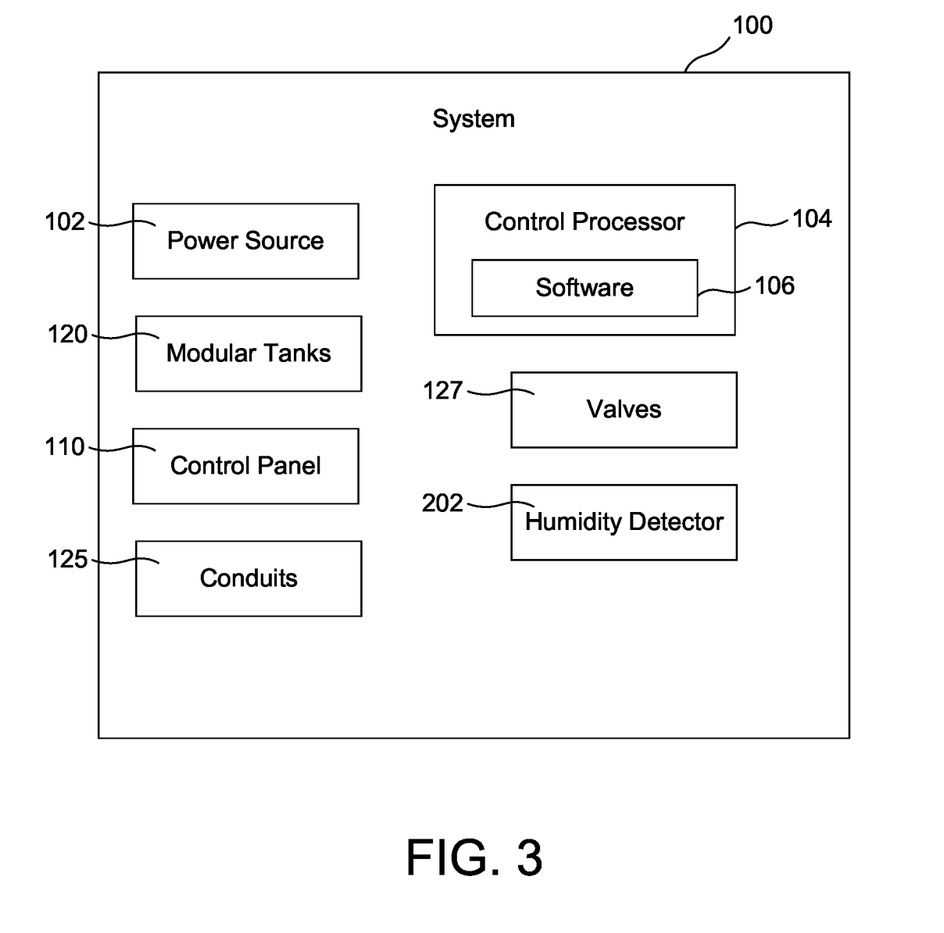
FIG. 3 is a schematic diagram illustrating an embodiment of a system for dry fogging in accordance with one or more embodiments of the present invention.
Figure 4:
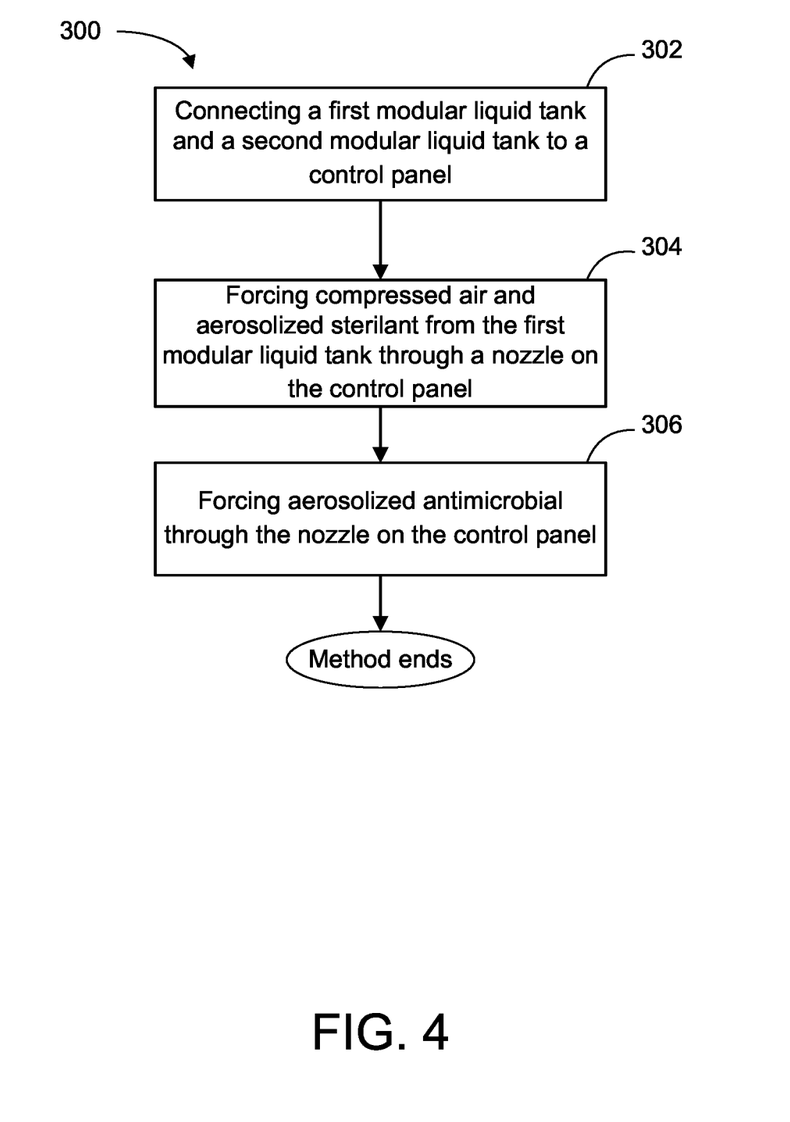
FIG. 4 is a flow chart diagram of a method for dry fogging in accordance with one or more embodiments of the present invention.
Figure 5:
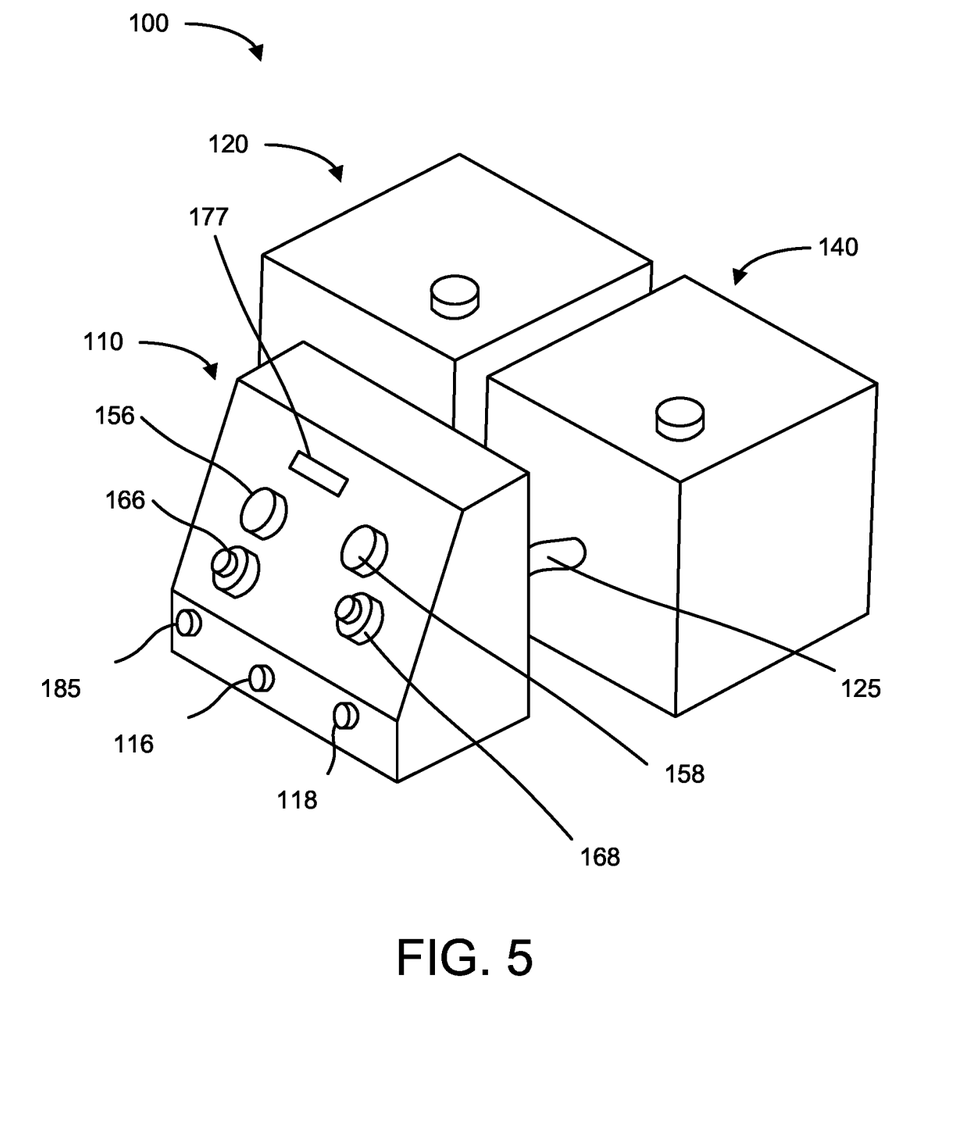
FIG. 5 is a schematic diagram illustrating an isometric view of an embodiment of a system for dry fogging in accordance with one or more embodiments of the present invention.

Referring to FIG. 3, a schematic diagram illustrating an embodiment of a system 100 for dry fogging is shown. Although shown and described with certain components and functionality, other embodiments may include fewer or more components to implement less or more functionality. The system 100 includes a control panel 110, at least one or a plurality of modular tanks 120.

In some embodiments, the modular tanks 120 are similar in size and shape and material, differing in only contents within their respective tanks. Different size modular tanks 120 may be modularly connected allowing one to provide more liquid for use. The modular tanks 120 are configured to attach and detach from the control panel 110. Modular components allow for their attachment and detachment to allow for ease in configuring and reconfiguring the system 100, which may include replacing components, shipping, servicing, and operating the components.

In some embodiments, the modular tanks 120 are made of a material that is suitable for the contents in the tank. The modular tanks 120 are configured to hold a pressure and resist excess heat transfer to or from the contents of the modular tanks 120. In some embodiments, the contents of the tank may include compressed air, a sterilant, a disinfectant, a sanitizer, an antimicrobial, or other similar substance that can be aerosolized. The contents of the tanks may vary depending on the application needed. In addition, the number of modular tanks 120 that are modularly connected to the control panel 110 may vary. The control panel 110 may be configured to dispense the contents of the modular tanks 120 in a sequential manner or at the same time. The modular tanks 120 may, in some embodiments, be connected to the control panel in any order as the connections are similar.

In other systems, the nozzle, port, or dispensing mechanism has been located on the tanks themselves. In some embodiments described herein, the control panel 110 includes a port, nozzle, or dispensing mechanism that is in communication with the contents of the tank such that the contents of the tank are aerosolized and dispensed from the port, nozzle, or dispensing mechanism. In some embodiments, the control panel 110 is configured to aerosolize the contents of the modular tanks 120. In some embodiments, the control panel 110 is configured to aerosolize the contents of the modular tanks 120 within the control panel 110 prior to dispensing through the port, nozzle, or dispensing mechanism.

In some embodiments, the modular tanks 120 are configured to be mechanically connected to the control panel 110. The control panel 110 may include valves 125, conduits 127, and other components that allow for the mixture of, the separating of, or the compartmentalizing of the contents from the various modular tanks 120. As such, the control panel 110 is, in some embodiments, configured to dictate the desired mixture of contents, the order of dispensing the contents, or the separation of dispensing of the contents of the modular tanks 120.

In some embodiments, the control panel 110 includes various components that are configured to monitor the modular tanks 120 and their contents. In some embodiments, the control panel is configured to measure the pressure of the contents of the modular tanks 120. This may include the air pressure or liquid pressure of the contents of the modular tanks 120. In some embodiments, the control panel 110 regulates the pressure of the contents of the modular tanks 120. The control panel 110 is configured to independently regulate the pressure of the individual modular tanks 120.

In some embodiments, the control panel 110 includes a user interface that is configured to allow a user to input conditions and manually operate the control panel 110 including the sequence of operation, the flow rate, the flow time, the concentration levels of sterilant, sanitizer, disinfectant, or antimicrobial that will be dispensed from the control panel 110. In some embodiments, these determinations are made automatically depending on the operating conditions of the system. Such factors including but not limited to the room size, the humidity, the temperature, the pressure, and the level of disinfecting needed may dictate the operating conditions of the system and may be automatically monitored and set based on an algorithm programmed into the control panel 110.

In some embodiments, the system 100 includes a control processor 104 and software 106. The control processor 104 is generally configured to control operations of the system 100 and the control panel 110, either alone or in conjunction with various processing sub-systems including the tanks and valves etc. of the overall system 100. For example, the control processor 104 might communicate electronically with the subsystems of the control panel 110 and the liquid tanks (see, for example, 120 and 140 of FIG. 1), as well as other any other system(s) included in various embodiments of the system 100.

The control processor 104 also includes software 106, in some embodiments, stored on any form of computer readable medium and accessible for execution by the control processor 104. The exact form or format of the software 106 is not constrained other than to be capable of performing the functions described herein and related functions within the scope of similar devices. In particular, the software 106 may be capable of carrying out part or all of the functionality described in any methods, steps, processes, or other functional descriptions of the system 100 and its component sub-systems.

Referring to FIG. 4, a method 300 for using a dry fogging machine is disclosed. The method 300 includes, at block 302, connecting a first modular liquid tank and a second modular liquid tank to a control panel. In some embodiments, the first modular liquid tank comprises compressed air and a liquid cold sterilant configured to disinfect and sterilize, and the second modular liquid tank comprises a liquid antimicrobial. At block 304, the compressed air and the aerosolized sterilant are forced through a first nozzle on the control panel. At block 306, an aerosolized antimicrobial is forced through a second nozzle on the control panel. In some embodiments, the first nozzle and the second nozzle are the same nozzle. In some embodiments, the first nozzle and the second nozzle are different nozzles. The method then ends.

Some embodiments may include only one or two of the depicted steps. In some embodiments, the forcing the compressed air and the liquid cold sterilant through the first nozzle occurs before the forcing the antimicrobial (or microbicide) through the second nozzle on the second modular liquid tank. In other embodiments, the forcing the compressed air and the liquid cold sterilant through the first nozzle occurs after the forcing the antimicrobial through the second nozzle on the second modular liquid tank.

In some embodiments, the method further includes independently regulating pressure in the first modular liquid tank and the second modular liquid tank with the control panel.

In some embodiments, the method further includes detaching one of the first modular liquid tank or the second modular liquid tank from the control panel. Detaching and reattaching may occur because the components are modular and can be reconfigured. In some embodiments, the first modular liquid tank and the second modular liquid tank may be switched in positioning relative to the control panel.

In some embodiments, the method further includes connecting a plurality of modular liquid tanks to the control panel. With a modular system a plurality of tanks may be connected to the control panel, allowing a multitude of options in setting up a dry fogging system.

Embodiments of apparatuses are described herein that may include on some of the features and components of the systems described. Additionally, other methods of using and making the systems described herein are contemplated.

Referring now to FIG. 5, an embodiment of a system 100 for dry fogging is shown. Although shown and described with certain components and functionality, other embodiments may include fewer or more components to implement less or more functionality. Also of note, while there are differences described between FIG. 5 and the some of the other Figures, each feature described with respect to FIGS. 1 through 4 may be individually or collectively added to the embodiments of FIG. 5. In addition, the features of FIG. 5 may be individually or collectively applied to any or all of FIGS. 1 through 4. The system 100 includes a first liquid tank 120 and a second liquid tank 140.

The liquid tanks (first liquid tank 120 and second liquid tank 140) are, in the illustrated embodiment, similar in size and shape and material, differing in only contents within their respective tanks. In some embodiments, the liquid tanks are different in size or shape allowing one or the other to provide more liquid for use. The liquid tanks are configured to attach and detach from the control panel 110. In some embodiments, the liquid tanks are modular. Modular components allow for their attachment and detachment to allow for ease in configuring the system 100, replacing components, shipping, servicing, and operating. If either of the liquid tanks require service, they can be detached and the system 100 can operate on the remaining liquid tank or a replacement tank.

In some embodiments, the liquid tanks are made of stainless steel or another material that is suitable for the contents in the tank. In some embodiments, the contents of the tank may include compressed air, a sterilant, or an antimicrobial. The contents of the tanks may vary depending on the application needed. In addition, the number of tanks that are modularly connected to the control panel 110 may vary. The control panel 110 may be configured to dispense the contents of the tanks in a sequential manner or at the same time. The control panel 110 may, in some embodiments, be configured to change the order of dispensing of the tanks.

In some embodiments, the control panel 110 includes various components that are configured to monitor the liquid tanks and their contents. In the illustrated embodiment, the control panel 110 contains no electronics. In such embodiments, the controls are all mechanical and/or pneumatic.

The illustrated embodiment includes a liquid port 116 (or a liquid connect) and an air port 118 (or air connect). The illustrated embodiment also includes a liquid gauge 156 and a liquid pressure regulator 166. The liquid gauge 156 and the liquid pressure regulator 166 are configured to monitor and regulate the liquid in the system. The illustrated embodiment also includes an air gauge 158 and an air pressure regulator 168. The air gauge 158 and the air pressure regulator 168 are configured to monitor and regulate the air in the system.

The illustrated embodiment also includes a selector switch 177. The selector switch is configured to designate which liquid is fed to a fog head. The illustrated embodiment also includes a flush valve 185. The flush valve 185 is configured to allow a user to flush a line without the necessity of emptying any tank.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The present subject matter may be embodied in other specific forms without departing from its spirit or essential characteristics. The described embodiments are to be considered in all respects only as illustrative and not restrictive.

In the above description, specific details of various embodiments are provided. However, some embodiments may be practiced with less than all of these specific details.

In other instances, certain methods, procedures, components, structures, and/or functions are described in no more detail than to enable the various embodiments of the invention, for the sake of brevity and clarity.

What is claimed is:

1. A system, comprising:
   a first liquid tank, comprising:
      compressed air and a first liquid configured to disinfect and sterilize;
   a second liquid tank, comprising a second liquid; and
   a control panel configured to regulate dispensing of the first liquid and the second liquid;
   wherein the first liquid tank, the second liquid tank, and the control panel are modular and configured to detach.

2. The system of claim 1, wherein the control panel further comprises a liquid port, wherein the liquid port is configured to dispense an aqueous form of the first liquid.

3. The system of claim 1, wherein the control panel further comprises a liquid port, wherein the liquid port is configured to dispense an aqueous form of the first liquid and an aqueous form of the second liquid.

4. The system of claim 1, wherein the control panel is configured to measure air pressure in the first liquid tank.

5. The system of claim 1, wherein the control panel is configured to measure air pressure within the first liquid tank.

6. The system of claim 1, wherein the control panel is configured to measure air pressure within the second liquid tank.

7. The system of claim 1 wherein the control panel is configured to regulate air pressure and liquid tank pressure independent of each other.

8. The system of claim 1, wherein the control panel is lined internally with heat tape.

9. The system of claim 1, wherein the first liquid tank and the second liquid tank are independently regulated by the control panel.

10. The system of claim 1, wherein the control panel is configured to be connected to a plurality of modular liquid tanks, wherein the first liquid tank and the second liquid tank are modular liquid tanks.

11. The system of claim 1, wherein the first liquid is a sterilant configured to disinfect and sterilize.

12. The system of claim 1, wherein the second liquid is a liquid antimicrobial.

13. An apparatus for controlling fog generation, the apparatus comprising:

a control panel configured to regulate a dispensing of an aerosolized or aqueous substance;
   a liquid port on the control panel configured to connect to at least one modular liquid tank and dispense the aerosolized substance from the at least one modular liquid tank; and
   an air port on the control panel configured to dispense a gas, wherein the control panel is configured to dispense the aqueous or aerosolized substance in combination with compressed air from the air port.

14. The apparatus of claim 13, wherein the liquid port on the control panel is configured to connect to at least two modular liquid tanks.

15. The apparatus of claim 13, wherein the aerosolized substance is produced by combining controllable air pressure and liquid pressure, and wherein the aerosolized substance comprises peracetic acid.

16. The apparatus of claim 13, wherein the liquid port is configured to dispense an aqueous substance from more than one modular liquid tank.

17. The apparatus of claim 13, wherein the control panel is configured to modularly connect to a plurality of liquid tanks, wherein the control panel is further configured to independently regulate each of the plurality of liquid tanks.

18. The apparatus of claim 13, wherein the control panel is configured to modularly connect to a plurality of liquid tanks, wherein the control panel is further configured to regulate air and liquid pressure in the first liquid tank and liquid pressure in the second liquid tank.

19. The apparatus of claim 13, wherein the control panel further comprises a remote humidity detector or a ppm detector.

20. A system, comprising:
   a first liquid tank, comprising:
      compressed air and a first liquid configured to disinfect and sterilize;
   a second liquid tank, comprising a second liquid;
   a control panel configured to regulate dispensing of the first liquid and the second liquid,
   wherein the control panel further comprises a liquid port, wherein the liquid port is configured to dispense an aqueous form of the first liquid and the second liquid, and
   wherein the first liquid tank, the second liquid tank, and the control panel are modular and configured to detach.

* * * * *